(12) United States Patent
Tanaka et al.

(10) Patent No.: US 8,202,247 B2
(45) Date of Patent: Jun. 19, 2012

(54) CAPSULE MEDICAL APPARATUS

(75) Inventors: Shinsuke Tanaka, Hino (JP); Hironao Kawano, Machida (JP); Hironobu Takizawa, Hino (JP); Miho Katayama, Yokohama (JP); Keita Suzuki, Tachikawa (JP)

(73) Assignee: Olympus Medical Systems Corp., Tokyo (JP)

( * ) Notice: Subject to any disclaimer, the term of this patent is extended or adjusted under 35 U.S.C. 154(b) by 57 days.

(21) Appl. No.: 12/772,319

(22) Filed: May 3, 2010

(65) Prior Publication Data

US 2010/0286668 A1 Nov. 11, 2010

Related U.S. Application Data

(63) Continuation of application No. PCT/JP2009/068849, filed on Nov. 4, 2009.

(30) Foreign Application Priority Data

Nov. 13, 2008 (JP) ................................. 2008-291444

(51) Int. Cl.
*A61M 5/00* (2006.01)
*A61M 37/00* (2006.01)
*A61K 9/22* (2006.01)
(52) U.S. Cl. .................. 604/115; 604/891.1; 604/890.1; 604/116; 604/93.01
(58) Field of Classification Search .................. 600/106, 600/583; 604/110, 115–119, 181, 187, 890.1, 604/891.1, 93.01; 607/133
See application file for complete search history.

(56) References Cited

U.S. PATENT DOCUMENTS

| 4,222,380 | A | * | 9/1980 | Terayama | 604/115 |
| 5,071,412 | A | | 12/1991 | Noda | |
| 5,531,692 | A | * | 7/1996 | Rogers | 604/110 |
| 6,706,000 | B2 | * | 3/2004 | Perez et al. | 600/583 |
| 2004/0158125 | A1 | * | 8/2004 | Aznoian et al. | 600/106 |
| 2004/0243211 | A1 | * | 12/2004 | Colliou et al. | 607/133 |
| 2005/0203547 | A1 | | 9/2005 | Weller et al. | |
| 2007/0179535 | A1 | | 8/2007 | Morrissey et al. | |
| 2008/0199065 | A1 | | 8/2008 | Swain | |

(Continued)

FOREIGN PATENT DOCUMENTS

JP 55-136040 10/1980

(Continued)

OTHER PUBLICATIONS

Japanese Office Action dated Jun. 15, 2010 with English translation.

(Continued)

*Primary Examiner* — Kevin C Sirmons
*Assistant Examiner* — Bradley Thomas, Jr.
(74) *Attorney, Agent, or Firm* — Scully, Scott, Murphy & Presser, P.C.

(57) ABSTRACT

A capsule medical apparatus includes a living tissue drawing portion in which a space for drawing the living tissue into a body of the capsule medical apparatus is formed; a movable unit that includes an engaging unit, which can be engaged with the living tissue of the subject, and that moves on a surface of the body of the capsule medical apparatus and in the living tissue drawing portion; an injection needle that has an ejection port for a drug and that protrudes such that the ejection port is positioned in the living tissue drawing portion; and an injection needle driver that drives the injection needle such that the injection needle protrudes.

13 Claims, 9 Drawing Sheets

U.S. PATENT DOCUMENTS

2009/0043278 A1   2/2009   Tanaka et al.
2009/0143697 A1   6/2009   Tanaka

FOREIGN PATENT DOCUMENTS

| | | |
|---|---|---|
| JP | S 55-136041 A | 10/1980 |
| JP | S 55-148540 A | 11/1980 |
| JP | S 55-166142 A | 12/1980 |
| JP | S 58-019232 A | 2/1983 |
| JP | S 58-019233 A | 2/1983 |
| JP | 2006-512108 | 4/2006 |
| JP | 2007-528263 | 10/2007 |
| JP | 2007-530129 | 11/2007 |
| JP | 2007-537817 | 12/2007 |
| JP | 2009-131415 | 6/2009 |
| WO | WO 2006/126653 A1 | 11/2006 |

OTHER PUBLICATIONS

International Search Report dated Dec. 8, 2009 with translation.

* cited by examiner

CAPSULE MEDICAL APPARATUS

CROSS-REFERENCE TO RELATED APPLICATION(S)

This application is a continuation of PCT international application Ser. No. PCT/JP2009/068849 filed on Nov. 4, 2009 which designates the United States, incorporated herein by reference.

BACKGROUND OF THE INVENTION

1. Field of the Invention

The present invention relates to a capsule medical apparatus that is introduced to a subject to inject a drug into a living tissue of the subject.

2. Description of the Related Art

In recent years, in the field of endoscopy, capsule body-insertable apparatuses (for example, capsule endoscopes) have been proposed that are provided with an imaging function and a radio communication function and body-insertable apparatus systems have been developed that acquire in-vivo images of a subject by using the capsule endoscope. A capsule endoscope is, for example, swallowed by a patient in order to observe (examine) the interior of the subject. Thereafter, the capsule endoscope moves through the body cavity, such as the internal organs including the stomach and the small intestine, by peristalsis of the internal organs until the capsule endoscope is naturally discharged and functions to capture in-vivo images of the subject at intervals of, for example, 0.5 second.

While the capsule endoscope moves through the inside of the subject, images that are captured by the capsule endoscope are received by an external image display device via antennae that are arranged on the body surface of the subject. The image display device has a function for communicating with the capsule endoscope by radio and an image memory function. The image display device sequentially stores the in-vivo images of the subject, which are received from the capsule endoscope, in a memory. A doctor or a nurse can observe (examine) the interior of the subject and diagnose the subject through display of the in-vivo images of the alimentary canal of the subject.

Japanese Laid-open Patent Publication No. 55-136040 describes a medical capsule apparatus in which a capsule is retained in the body. A living tissue is aspirated into the capsule using an aspiration tube that communicates with the outside of the body. Living tissue is punctured with a retainment pin in order to retain the capsule in the body.

SUMMARY OF THE INVENTION

A capsule medical apparatus according to an aspect of the present invention is a capsule medical apparatus that is introduced into a subject and injects a drug into a living tissue of the subject. The capsule medical apparatus includes a living tissue drawing portion in which a space for drawing the living tissue into a body of the capsule medical apparatus is formed; a movable unit that includes an engaging unit, which can be engaged with the living tissue of the subject, and that moves on a surface of the body of the capsule medical apparatus and in the living tissue drawing portion; an injection needle that has an ejection port for a drug and that protrudes such that the ejection port is positioned in the living tissue drawing portion; and an injection needle driver that drives the injection needle such that the injection needle protrudes.

A capsule medical apparatus according to another aspect of the present invention is a capsule medical apparatus that is introduced into a subject and injects a drug into a living tissue of the subject. The capsule medical apparatus includes a living tissue drawing means in which a space for drawing the living tissue into a body of the capsule medical apparatus is formed; a movable means including an engaging unit which can be engaged with the living tissue of the subject, the movable means being for moving on a surface of the body of the capsule medical apparatus and in the living tissue drawing means; an injection needle that has an ejection port for a drug and that protrudes such that the ejection port is positioned in the living tissue drawing means; and an injection needle driving means for driving the injection needle such that the injection needle protrudes.

The above and other features, advantages and technical and industrial significance of this invention will be better understood by reading the following detailed description of presently preferred embodiments of the invention, when considered in connection with the accompanying drawings.

DETAILED DESCRIPTION OF THE PREFERRED EMBODIMENTS

Preferred embodiments of a capsule medical apparatus according to the present invention will be explained in detail below with reference to the drawings. The present invention is not limited to the embodiments.

First Embodiment

Figure 1:
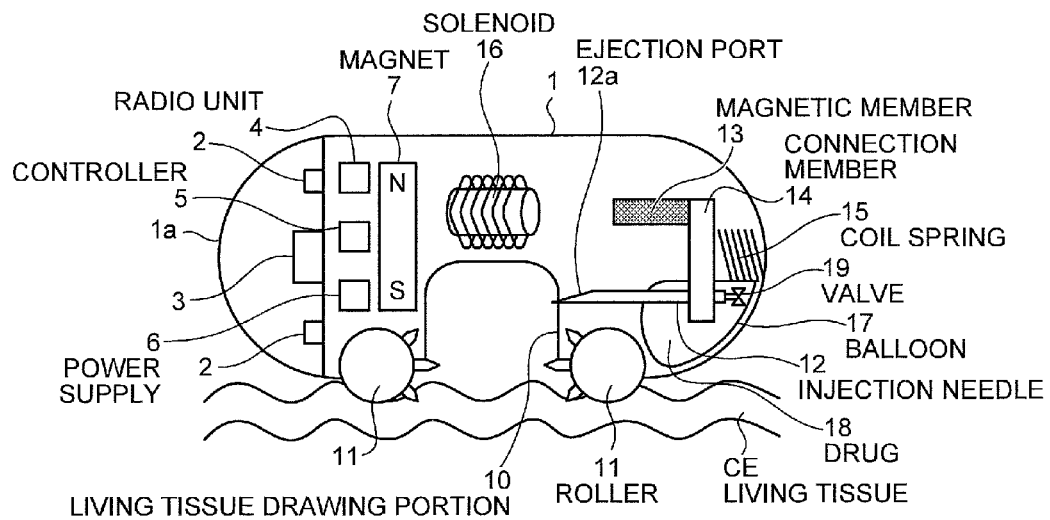
FIG. 1 is a schematic diagram of a configuration of a capsule medical apparatus according to a first embodiment of the present invention.

FIG. 1 is a schematic diagram of a configuration of a capsule medical apparatus according to a first embodiment of the present invention. As illustrated in FIG. 1, the capsule medical apparatus is a capsule-shaped medical apparatus that is formed in a size such that the capsule medical apparatus can be introduced into a subject. The capsule medical apparatus is introduced to the subject, draws a desired living tissue into the capsule medical apparatus, injects a drug into the drawn living tissue, and then releases the drawn living tissue to which the drug has been injected.

One open end of the cylindrical casing of the capsule medical apparatus is sealed with a transparent dome-shaped casing 1a and a capsule-shaped casing 1, which is kept watertight, contains various functions. The capsule medical apparatus includes an imaging unit 3 on the axis of the capsule-shaped casing 1 and in the vicinity of the dome-shaped casing 1a. The imaging unit 3 is realized using an imaging device and a condenser optical system and captures in-vivo images of the subject. Furthermore, illuminating units 2, which are annularly arranged, and are realized using, for example, LEDs, are arranged on the radially outward side with respect to the imaging unit 3.

The cylindrical casing of the capsule-shaped casing 1 has a living tissue drawing portion 10 in which a space is formed into which a desired living tissue CE is taken from a side portion. The cylindrical casing further has a pair of rollers 11 that serves as a living tissue moving unit that moves the living tissue CE into the living tissue drawing portion 10. The rollers 11 are rotatable in an arbitrary direction. The rollers 11 have claws on their circumference and draw the living tissue CE outside the capsule-shaped casing 1 into the living tissue drawing portion 10. An injection needle 12 that punctures the living tissue CE, which is drawn into the living tissue drawing portion 10, is provided in the capsule-shaped casing 1. The injection needle 12 has an ejection port 12a, the tip of which is obliquely cut.

The injection needle 12 is connected to a magnetic member 13 via a connection member 14. A solenoid 16 is provided in a position opposed to the magnetic member 13. When the solenoid 16 is energized, it attracts the magnetic member 13. By energizing the solenoid 16, the injection needle 12 is made to protrude to the living tissue drawing portion 10 and the ejection port 12a can be positioned in a desired position in the living tissue drawing portion 10. A coil spring 15, which is a compression spring for pulling back the connection member 14, is connected to the connection member 14. The magnetic member 13, the connection member 14, the coil spring 15, and the solenoid 16 serve as an injection needle driver that drives the injection needle 12 such that the injection needle 12 protrudes.

Furthermore, a balloon 17 that stores a drug 18 is provided in the capsule-shaped casing 1. The balloon 17 is connected to the injection needle 12 via a valve 19. By opening the valve 19, the drug 18 in the balloon 17 is pushed out through the injection needle 12 by the contractile force of the balloon 17 and the drug 18 can thus be ejected from the ejection port 12a.

The capsule-shaped casing 1 contains a magnet 7, the magnetization direction of which is set in a radial direction, and that serves as a magnetic member that enables axial rotation and translational movement of the capsule medical apparatus in accordance with the application of an external magnetic field; a radio unit 4 that transmits by radio various types of information including in-vivo images, which are captured by the imaging unit 3, to the outside of the subject; a controller 5 that controls processes on various components in the capsule-shaped casing 1; and a power supply 6 that supplies electric power to the various components in the capsule-shaped casing 1.

Figure 2:
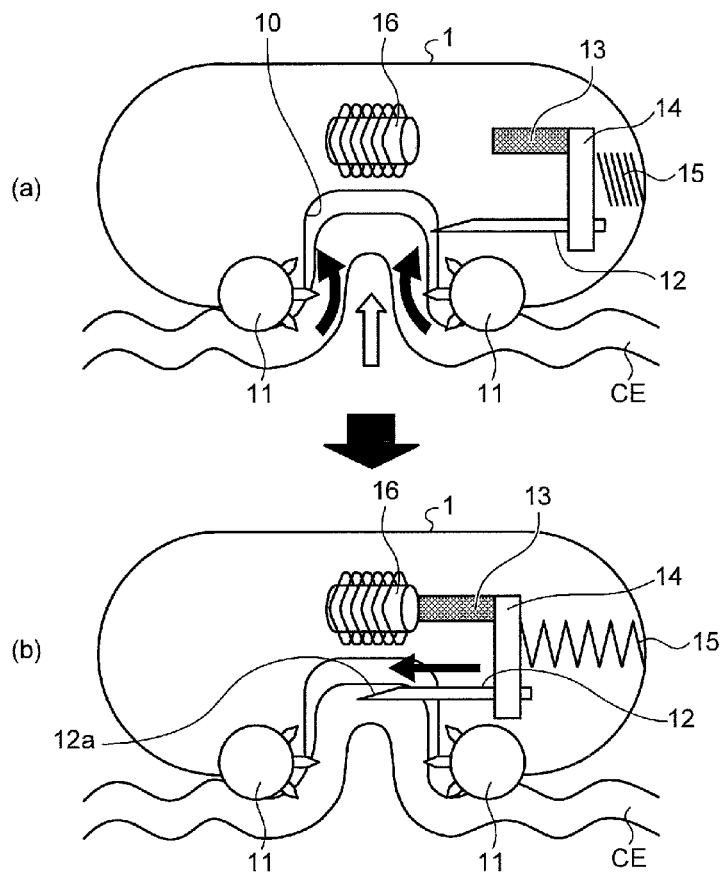
FIG. 2 is a schematic diagram explaining operations for drawing a living tissue and operations for puncturing a living tissue, which are performed by the capsule medical apparatus illustrated in FIG. 1.

A process for taking a living tissue and a process for injecting a medical agent, which are performed by the capsule medical apparatus illustrated in FIG. 1, will be explained with reference to FIG. 2 and FIG. 3. First, the controller 5 transmits in-vivo images of the subject, which are sequentially captured by the imaging unit 3, to the outside of the subject via the radio unit 4. An operator observes the transmitted in-vivo images outside the subject and determines whether the capsule medical apparatus has reached the position of a living tissue to which the drug is to be injected. When the capsule medical apparatus has reached the position, a magnetic field is applied from the outside in order to activate a magnetic switch (not shown) in order to start the process for injecting the drug into the living tissue. The capsule medical apparatus may be moved actively. For example, the capsule medical apparatus may be rotated or moved linearly by generating a rotation magnetic field or an oblique magnetic field from the outside. The process for injecting the drug into the living tissue may be started by a receiving unit that is provided in the capsule medical apparatus and instruction signals that are transmitted from the outside. Furthermore, the process for injecting the drug into the living tissue may be started by a capsule medical apparatus that is provided with a pH sensor, or the acquired in-vivo images may be analyzed, in order to detect autonomously whether the capsule medical apparatus has almost reached a target in the body.

Once an instruction is issued for starting the process for injecting the drug into the living tissue, the controller 5 rotates the rollers 11 and the living tissue CE is taken into the living tissue drawing portion 10, as illustrated in FIG. 2(a). Once drawing of the living tissue CE into the living tissue drawing portion 10 finishes, the controller 5 stops the rollers 11 rotating so that the living tissue CE is stored in the living tissue drawing portion 10. Thereafter, as illustrated in FIG. 2(b), the controller 5 energizes the solenoid 16 to attract the magnetic member 13 so that the injection needle 12 is caused to protrude and puncture the living tissue CE in the living tissue drawing portion 10. In this case, the ejection port 12a of the injection needle 12 is controlled so that it is positioned approximately at the center of the living tissue drawing portion 10 with respect to the width of the living tissue drawing portion 10. Thereafter, the controller 5 opens the valve 19, the drug 18 in the balloon 17 is pushed out through the injection needle 12, and the drug 18 is injected from the ejection port 12a into the living tissue CE. After injection of the drug 18 is finished, the controller 5 stops energizing the solenoid 16 and pulls out the injection needle 12 from the living tissue CE and returns it to its original position using the compression force of the coil spring 15. Thereafter, the controller 5 reverses the rotation of the rollers 11 in order to draw back the living tissue CE, which is drawn into the living tissue drawing portion 10 and to which the medical agent 18 is injected, to the outside.

Figure 3:
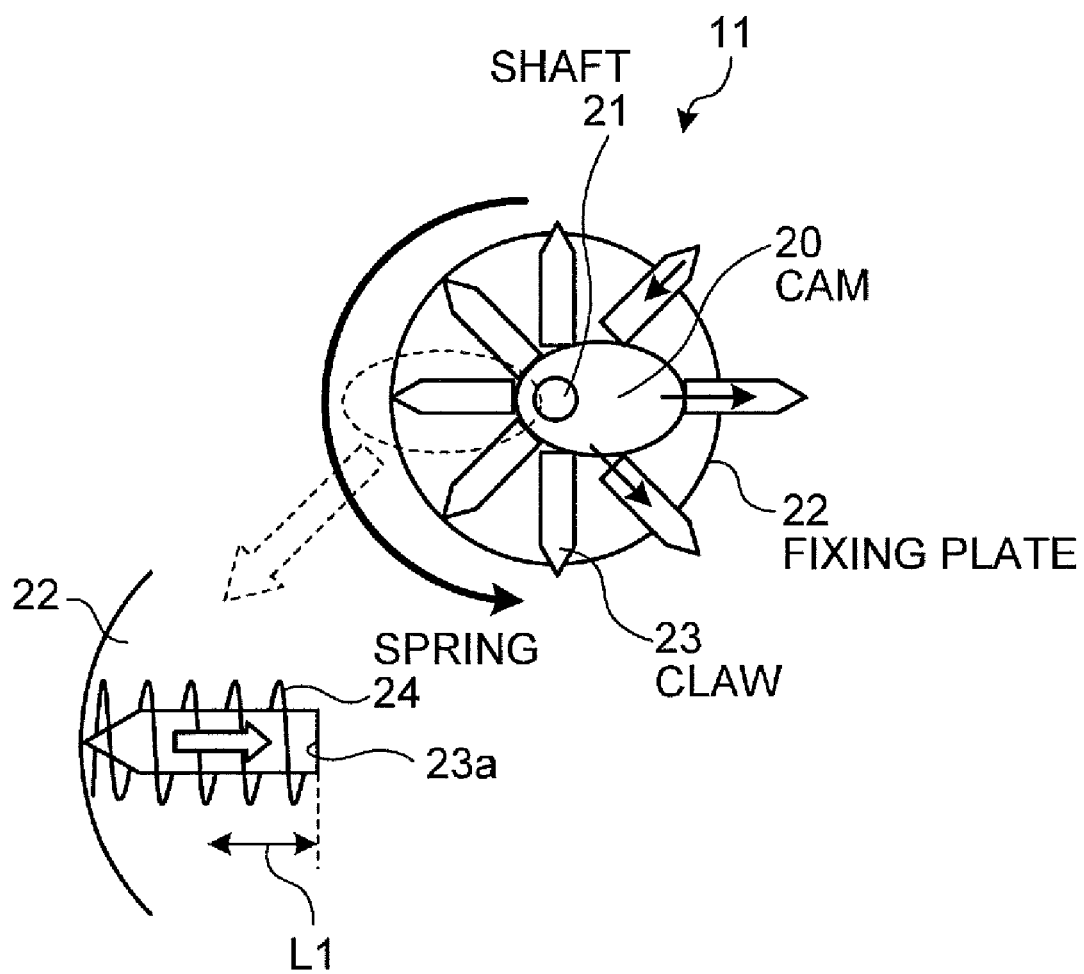
FIG. 3 is a schematic diagram of a detailed configuration of a roller.

Specifically, as illustrated in FIG. 3, in the roller 11, claws 23 that radially move in and out to and from a shaft 21, which is the rotation shaft, are arranged circumferentially on one side of a discoid fixing plate 22. The radially outward tips of the claws 23 are tapered so as to catch the living tissue CE. The outer surface of each of the claws 23 is covered with a coiled spring 24 and is inserted in the internal coil space of the spring 24. The radially outward ends of the springs 24 are fixed around the circumference of the fixing plate 22, and the radially inward ends on the other side are connected to the base ends 23a of the claws 23. A cam 20 is arranged on the shaft 21. The base ends 23a of the claws 23 are pressed against the circumference of the cam 20 at a predetermined distance L1 by the pressing force of the spring 24, which serves as a compression spring. When the protrusion of the cam 20 makes contact with the base end 23a of the claw 23, the tip portion of the claw 23 protrudes from the circumference of the fixing plate 22. The rotation of the fixing plate 22 on the shaft 21 causes each of the tip portions of the claws 23 to sequentially protrude in the rotation direction, and the tip portion captures the living tissue CE and catches it in the rotation direction of the fixing plate 22. It is preferable that, when the living tissue CE is not drawn in, the position at which the cam 20 stops be set such that the claws 23 do not protrude from the outer circumference surface of the capsule-shaped casing 1 in order not to prevent the movement of the capsule medical apparatus.

In the first embodiment, the living tissue CE is drawn into the living tissue drawing portion 10. The injection needle 12 is caused to protrude toward the drawn living tissue CE in the width direction of the living tissue drawing portion 10 in order to puncture the living tissue CE such that the ejection port 12a of the injection needle 12 is positioned at approximately the center of the living tissue drawing portion 10, and then the drug 18 is injected. Accordingly, puncturing of the living tissue CE with the injection needle 12 and injection of the drug 18 into the living tissue CE can be definitely performed.

Modification 1 of First Embodiment

Modification 1 of the first embodiment of the present invention will be explained below. In Modification 1 of the first embodiment, as illustrated in FIG. 4(a), a pair of electrodes 25, which serves as a detecting unit that detects drawing of the living tissue CE, is provided near the bottom of the living tissue drawing portion 10 so that the living tissue CE can be punctured with the injection needle 12 more definitely.

Figure 4:
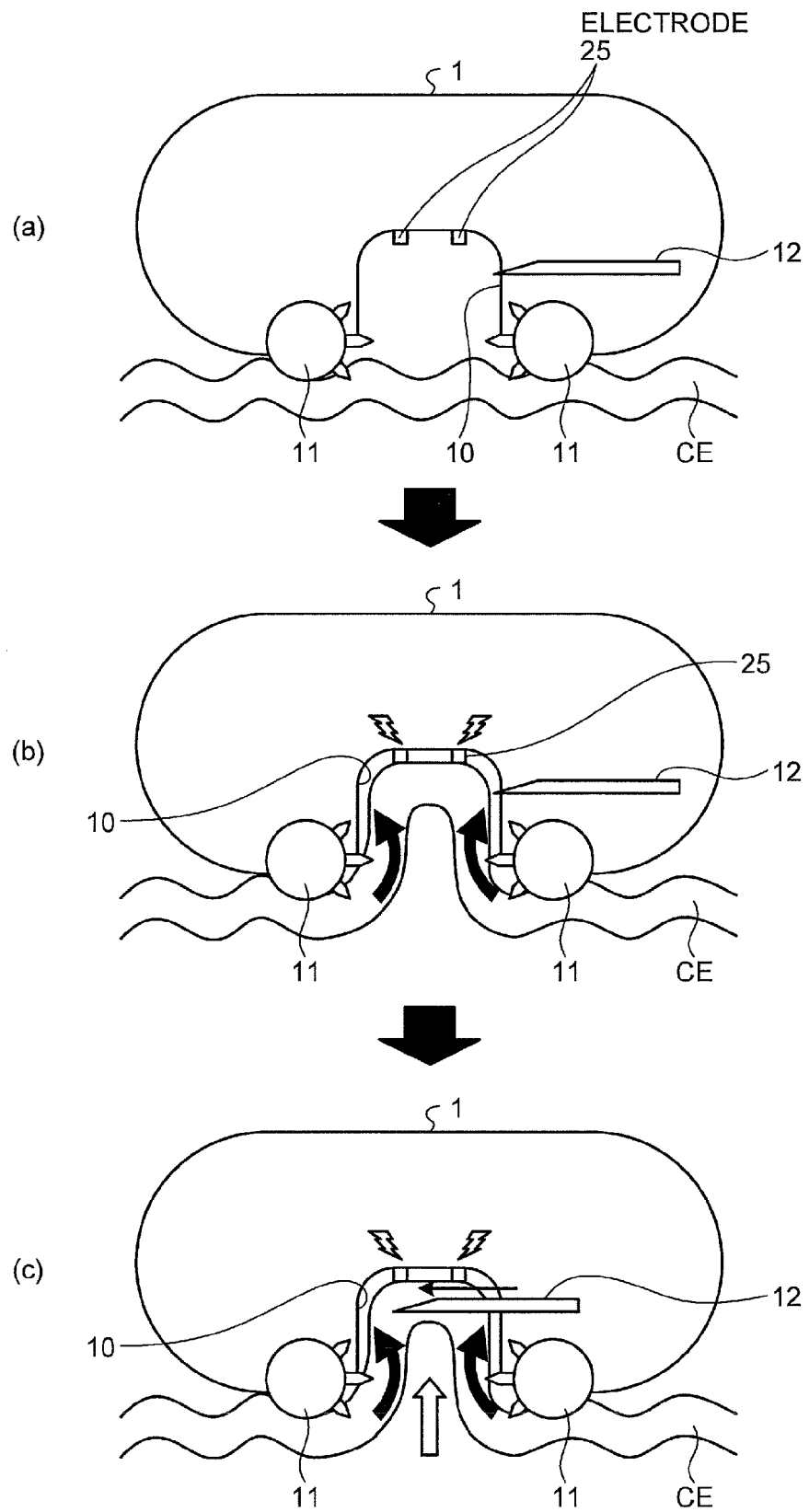
FIG. 4 is a schematic diagram illustrating a configuration and operations of a capsule medical apparatus according to Modification 1 of the first embodiment of the present invention.

As illustrated in FIG. 4(b), when the living tissue CE is drawn into the living tissue drawing portion 10 in accordance with the rotation of the rollers 11, electricity is conducted in the vicinity of the pair of electrodes 25 because of, for example, the body fluid. The pair of electrodes 25 can detect conduction by measuring the resistance or conductivity between the electrodes 25. When conduction is detected, it can be determined that the living tissue is being drawn into the living tissue drawing portion 10.

When the pair of electrodes 25 detects that the living tissue CE is drawn in, as illustrated in FIG. 4(b), the controller 5 stops rotation of the rollers 11, causes the injection needle 12 to protrude in the width direction of the living tissue drawing portion 10 and puncture the living tissue CE, and the drug 18 is injected.

In Modification 1 of the first embodiment, it can be confirmed, using the pair of electrodes 25, whether the living tissue CE is in a position where it can be punctured. Thus, if the living tissue CE cannot be drawn in accordance even with the rotation of the roller 11, the living tissue CE can be punctured with the injection needle 12 definitely without extra protruding operations of the injection needle 12.

It can be detected whether the living tissue CE is in the position where can be punctured using, instead of the pair of electrodes 25, for example, a pressure-sensitive contact sensor, an optical sensor that includes a light emitter and a light receiver and detects variations in reflectance or variations in transmittance because of the living tissue CE, a force sensor that measures a repulsion from the living tissue CE when the injection needle 12 protrudes, or a pressure sensor that detects a liquid pressure of the drug 18, such as a medical agent, to be supplied through the injection needle 12.

Second Embodiment

Figure 5:
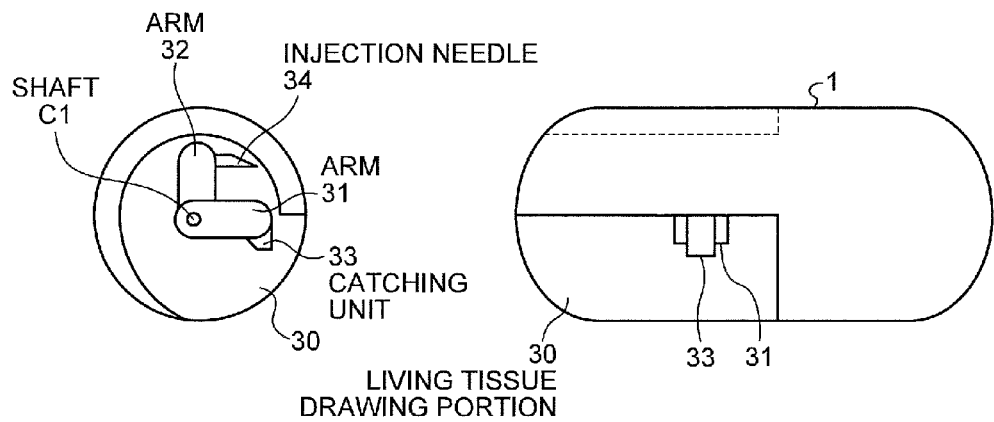
FIG. 5 is a schematic diagram of a configuration of a capsule medical apparatus according to a second embodiment of the present invention.

A second embodiment of the present invention will be explained below. In the second embodiment, as illustrated in FIG. 5, a living tissue drawing portion 30, which corresponds to the living tissue drawing portion 10, in the capsule-shaped casing 1 has a shape like a column that is partly open. A catching unit 33 is provided for the tip portion of an arm 31 that rotates on the shaft C1 of the column, and an injection needle 34 is attached to the tip portion of an arm 32 that is approximately orthogonal to the arm 31 and rotates in the rotation direction with a lag of 90 degrees. The direction of the puncture with the injection needle 34 is in the circumferential direction of the rotation direction. In other words, the injection needle 34 is pointing at a tangent to the rotation track of the tip of the arm 32. The ejection port of the injection needle 34 is provided at its tip.

Figure 6:
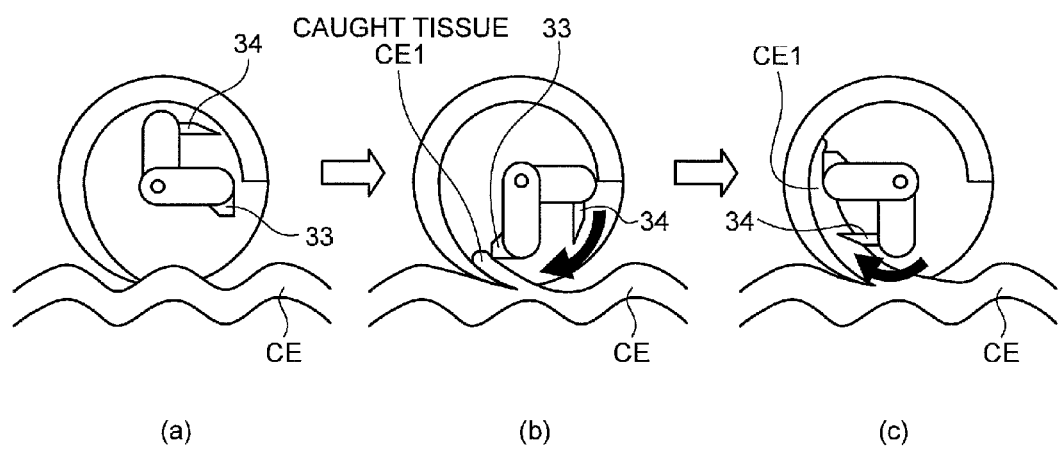
FIG. 6 is a schematic diagram of operations for drawing a living tissue and operations for puncturing a living tissue, which are performed by the capsule medical apparatus according to the second embodiment of the present invention.

As illustrated in FIGS. 6(a) and 6(b), when the arms 31 and 32 rotate on the shaft C1 such that the arms 31 and 32 precede in the rotation direction, the catching unit 33, which is attached to the tip of the arm 31, catches the living tissue CE from the opening and draws a caught tissue CE1 into the living tissue drawing portion 30. Thereafter, as illustrated in FIG. 6(c), the injection needle 34 rotates lagging behind the catching unit 33 and punctures the caught tissue CE1, and the drug is injected once the arms 31 and 32 stop rotating. The caught tissue CE1 is released to the outside of the capsule-shaped casing 1 by reversing the rotation of the arms 31 and 32. The angle formed by the arms 31 and 32 may be appropriately changed in accordance with the catching of the living tissue CE.

In the second embodiment, rotation of the arms 31 and 32 allows the drawing operations and the puncture operations through one operation, i.e., rotation.

Figure 7:
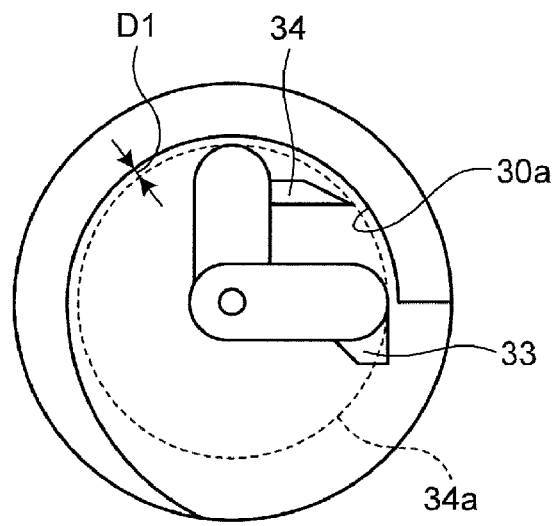
FIG. 7 is a lateral cross-sectional schematic diagram of a configuration of the capsule medical apparatus according to the second embodiment of the present invention.

In the second embodiment, as illustrated in FIG. 7, a circular trace 34a of the ejection port of the injection needle 34 is formed such that a certain interval D1 is kept between the circular trace 34a and an inner wall 30a of the living tissue drawing portion 30. Accordingly, the position where the caught tissue CE1 is punctured is a position with a predetermined depth. Furthermore, because the caught tissue CE1 is punctured in the circumferential direction, the definite puncture position with the predetermined depth can be achieved and the drug can be injected at the position for the predetermined depth definitely.

Modification 1 of Second Embodiment

Figure 8:
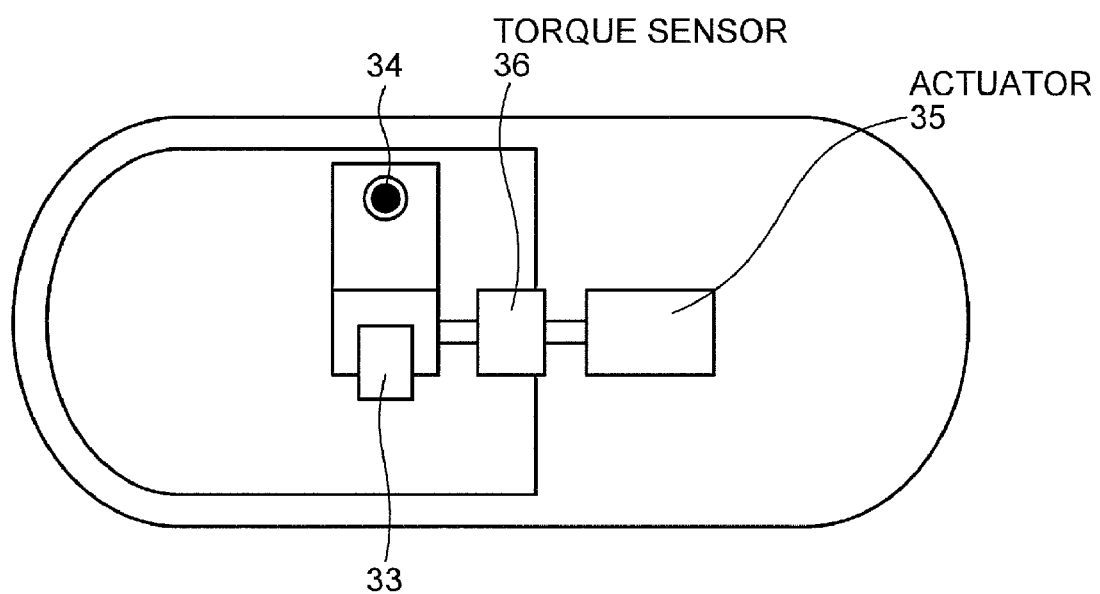
FIG. 8 is a longitudinal cross-sectional schematic diagram of a configuration of a capsule medical apparatus according to Modification 1 of the second embodiment of the present invention.

Drawing of the living tissue CE may be detected according to Modification 1 of the first embodiment. For example, as illustrated in FIG. 8, a torque sensor 36 that detects the torque of rotation may be provided on the shaft C1 of an actuator 35, such as a motor that causes the arms 31 and 32 to rotate on the shaft C1. When the torque is a predetermined value or larger, it is determined that the living tissue CE is drawn in.

Third Embodiment

A third embodiment of the present invention will be explained below. In both of the first and second embodiments, the living tissue CE is drawn using a rotation mechanism. In the third embodiment, the living tissue CE is drawn using an aspiration mechanism.

Figure 9:
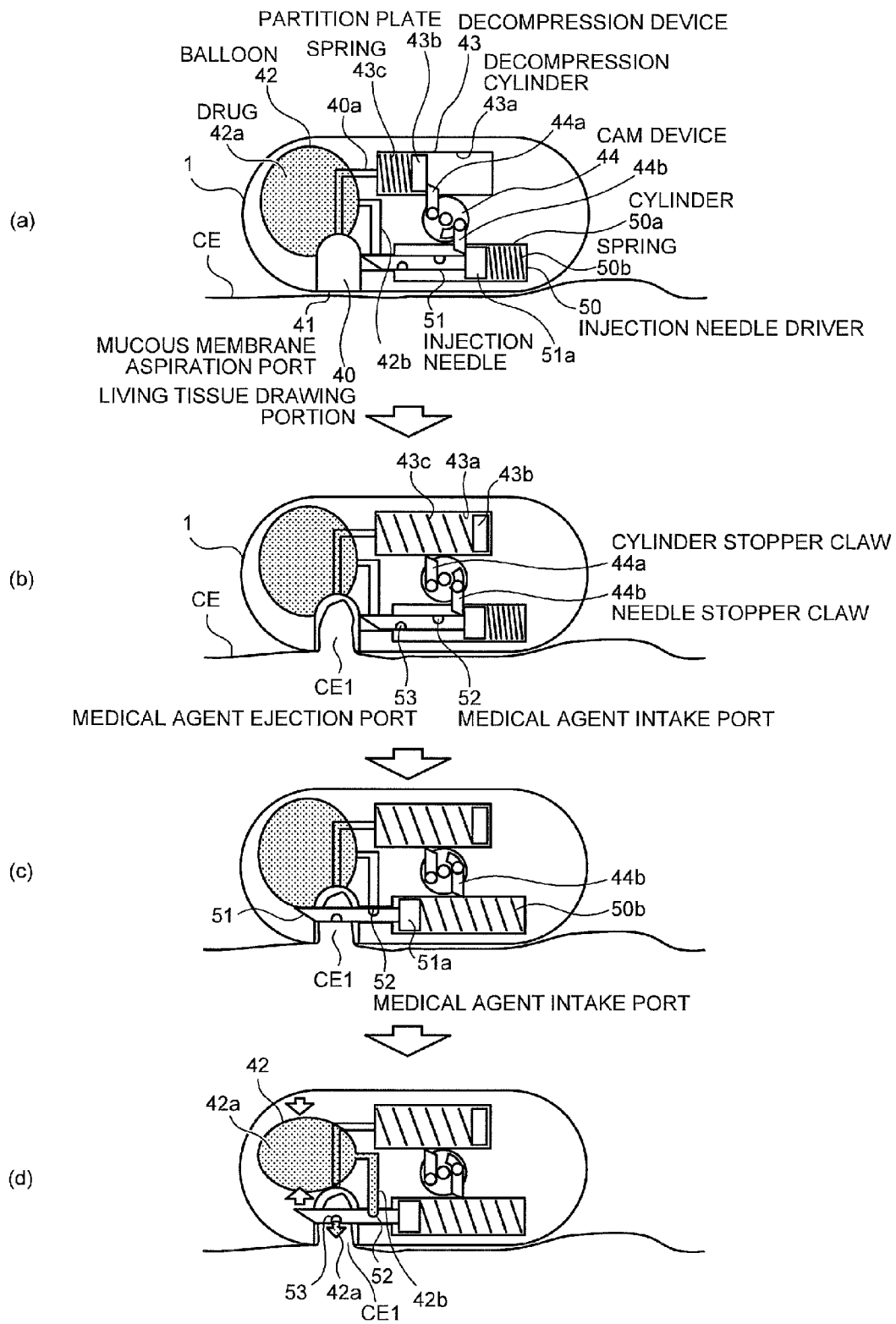
FIG. 9 is a schematic diagram of a configuration of a capsule medical apparatus according to a third embodiment of the present invention.

FIG. 9 is a schematic diagram of a schematic configuration of a capsule medical apparatus according to a third embodiment of the present invention. The capsule medical apparatus includes a living tissue drawing portion 40, which corresponds to the living tissue drawing portion 10. A mucous membrane aspiration port 41 through which the living tissue CE is drawn is formed in the capsule-shaped casing 1. The capsule-shaped casing 1 contains a decompression device 43 that draws the living tissue CE into the living tissue drawing portion 40 by aspiration, an injection needle driver 50 that causes an injection needle 51 to protrude to a predetermined position in the living tissue drawing portion 40, a cam device 44 that controls the timing at which the decompression device 43 and the injection needle driver 50 operate, and a balloon 42 that stores a drug 42a.

To draw in the living tissue CE, as illustrated in FIGS. 9(a) and 9(b), the capsule medical apparatus removes restriction on a partition plate 43b in the decompression device 43 with a cylinder stopper claw 44a in accordance with the rotation of the cam device 44. In a decompression cylinder 43a of the decompression device 43, an extensible spring 43c that is provided on the side of the living tissue drawing portion 40 is kept compressed by the partition plate 43b. Once the partition plate 43b is released, the spring 43c extends and thus the inside of the living tissue drawing portion 40, which is connected via a connection pipe 40a, is decompressed. Accordingly, the living tissue CE, which is brought into contact with the capsule-shaped casing 1, in the vicinity of the mucous membrane aspiration port 41 is drawn as a caught tissue CE1 into the living tissue drawing portion 40.

The cam device 44 performs operations for drawing a needle stopper claw 44b lagging behind the drawing of the cylinder stopper claw 44a. The injection needle driver 50 causes the injection needle 51 to be inserted into a cylinder 50a and causes the injection needle 51 to protrude toward the living tissue drawing portion 40. In the cylinder 50a, an extendable spring 50b is kept compressed between a bottom 51a of the injection needle 51 and the bottom of the cylinder 50a by the needle stopper claw 44b. Once the bottom 51a of the injection needle 51 is released in accordance with the drawing of the needle stopper claw 44b, the injection needle 51 protrudes to the living tissue drawing portion 40 due to a pressing force caused by the extension of the spring 50b.

A medical agent ejection port 53 is formed on the side surface of the tip of the injection needle 51 and a medical agent intake port 52 is formed on the side surface of the base end of the injection needle 51. The medical agent ejection port 53 and the medical agent intake port 52 are communicated with each other via the narrow tubular injection needle 51. The tip of the injection needle 51 is cut and formed such that puncture operation is easily performed. However, the tip is sealed so that the drug is not ejected. When the injection needle driver 50 causes the injection needle 51 to protrude to the living tissue drawing portion 40, the injection needle 51 protrudes such that the medical agent ejection port 53 is positioned approximately at the center of the living tissue drawing portion 40 and the medical agent intake port 52 is positioned such that it can be connected to the ejection port of a connection pipe 42b that connects the medical agent intake port 52 to the balloon 42. Accordingly, after the injection needle 51 finishes the protruding operations, i.e., the puncture operations, the contractile force of the balloon 42 causes the drug 42a to be injected from the medical agent ejection port 53 to the caught tissue CE1 via the connection pipe 42b and the medical agent intake port 52, as illustrated in FIG. 9(d).

In the third embodiment, an aspiration mechanism draws the living tissue CE and the cam device 44 adjusts the timing at which the living issue CE is drawn and the operations for puncturing with the injection needle 51 are adjusted. Therefore, the timing for operations for taking the living tissue CE and the injection needle 51 can be automatically performed using a simple device.

Furthermore, a medical agent ejection port 53 is provided on a side portion of the injection needle 51. This reduces the diameter of the ejection port and increases the accuracy in positioning the injection of the medical agent into a surfaces layer, such as a thin mucous membrane, compared with the case where the ejection port is provided at the tip cut portion.

Modification 1 of Third Embodiment

Figure 10:
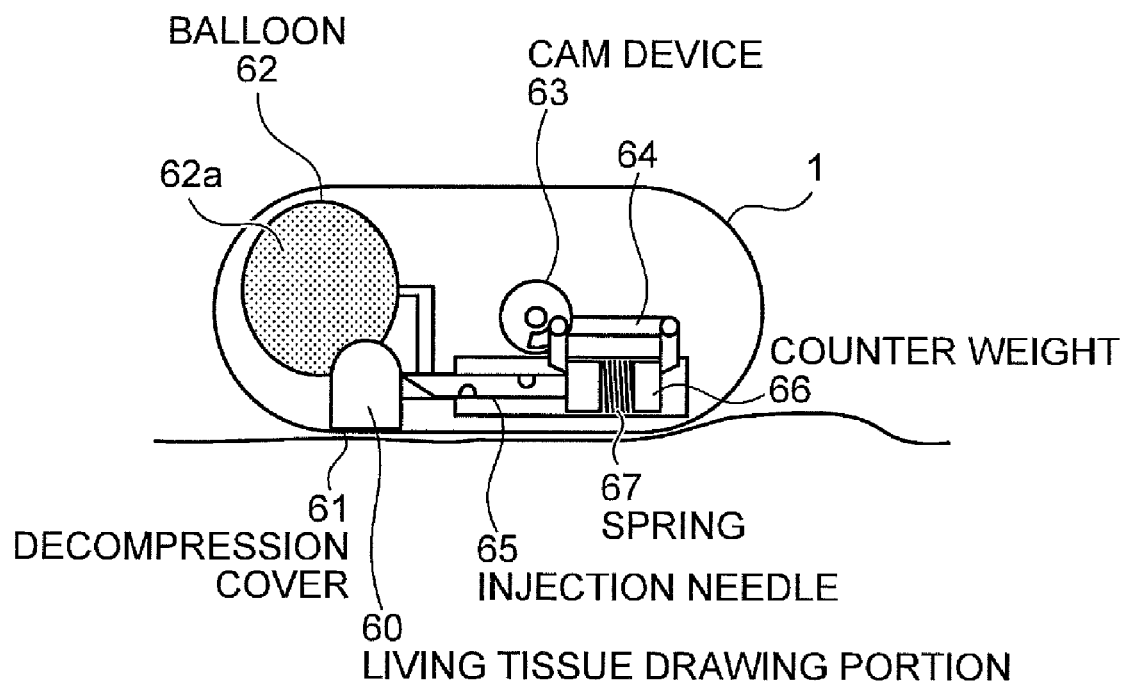
FIG. 10 is a schematic diagram of a configuration of a capsule medical apparatus according to Modification 1 of the third embodiment of the present invention.

Modification 1 of the third embodiment of the present invention will be explained below. In Modification 1 of the third embodiment, as illustrated in FIG. 10, the opening of a living tissue drawing portion 60, which corresponds to the living tissue drawing portion 40, is closed with a decompression cover 61. Furthermore, the decompression device 43 illustrated in FIG. 9 is removed. The inside of the living tissue drawing portion 60 is decompressed beforehand.

The decompression cover 61 may be formed of a material that dissolves in, for example, the body fluid in a living body such that it opens or may be opened using an actuator (not illustrated). The actuator (not illustrated) may be a magnetic actuator that opens in accordance with an external magnetic field.

Puncturing with an injection needle 65 is performed using a cam device 63 to release a stopper claw 64. The injection needle 65 is inserted into a cylinder like the cylinder 50a. The compressed spring 67 is kept sandwiched between the bottom of the injection needle 65 and a counter weight 66, which is provided on the bottom of the cylinder. This state is maintained in a way that the bottom of the injection needle 65 and the counter weight 66, which sandwich the spring 67, are sandwiched between the stopper claws 64 of the cam device 63. By releasing the stopper claws 64, the injection needle 65 is caused to protrude and puncture the living tissue CE in the living tissue drawing portion 60. The counter weight 66 moves to the side opposite to the direction in which the injection needle 65 protrudes. Accordingly, the capsule-shaped casing 1 exerts no repulsion when the injection needle 65 protrudes, and thus the capsule-shaped casing 1 does not deviate, so stable puncture operations of the injection needle 65 can be performed. Thereafter, a drug 62a, as the drug 42a according to the third embodiment, in a balloon 62 is injected into the living tissue CE in the living tissue drawing portion 60 via the injection needle 65 due to the contractile force of the balloon 62.

In Modification 1 of the third embodiment, the operations for drawing the living tissue CE can be performed and the puncture operations of the injection needle 65 can be stably performed using a simple configuration.

Modification 2 of Third Embodiment

Modification 2 of the third embodiment of the present invention will be explained below. In the third embodiment, the inside of the living tissue taking portion 40 is decompressed using the decompression device 43 in order to take in the living tissue CE. In Modification 2 of the third embodiment, instead of using the decompression device 43, the injection needle driver is provided with a decompression mechanism.

Figure 11:
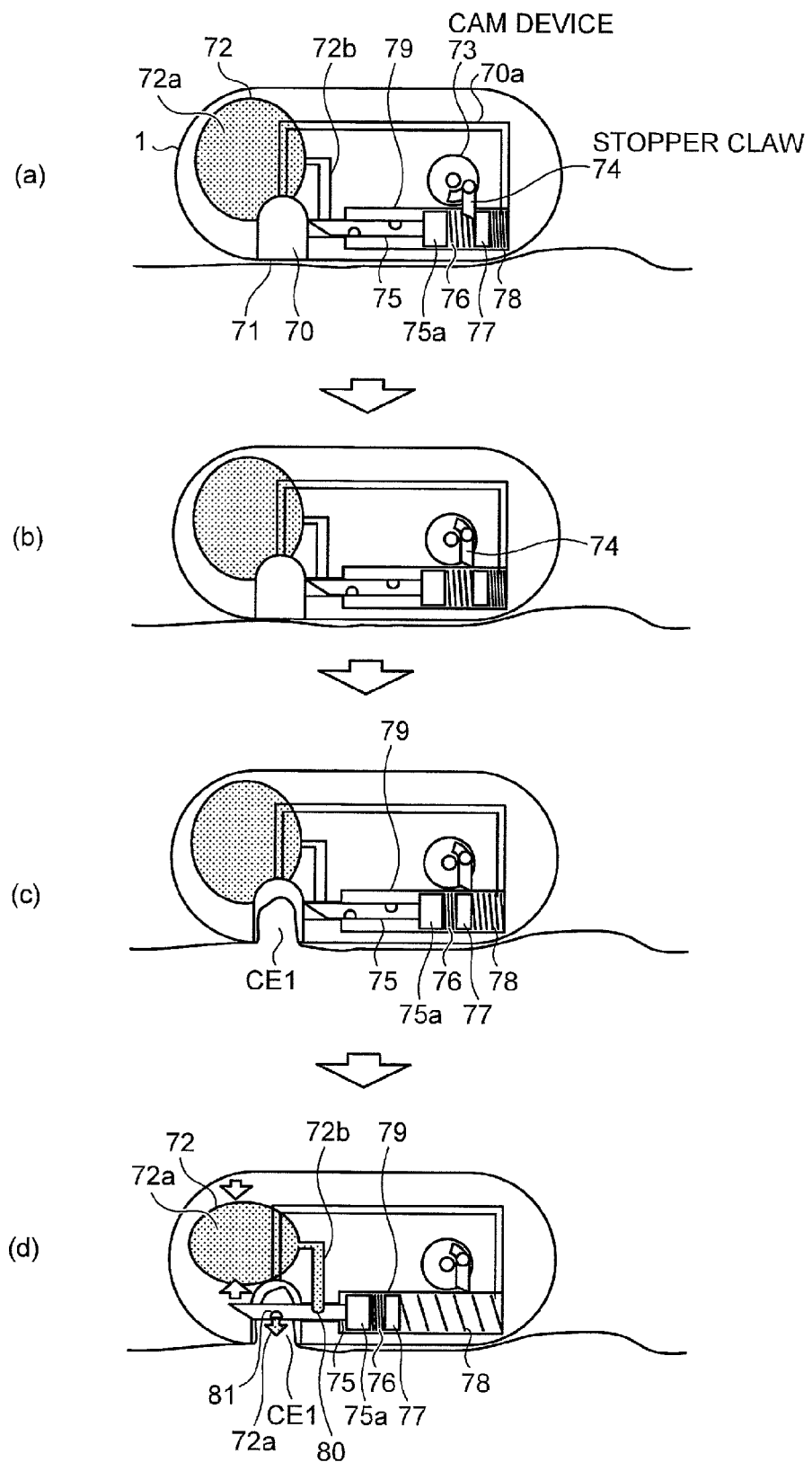
FIG. 11 is a schematic diagram of a configuration of a capsule medical apparatus according to Modification 2 of the third embodiment of the present invention.

In other words, as illustrated in FIG. 11(a) an extensible spring 78, a partition plate 77, a spring 76, and an injection needle 75 that has a bottom portion 75a are inserted sequentially into the cylinder of an injection needle driver 79 from the bottom portion. The space in which the spring 78 in the vicinity of the bottom of the cylinder is inserted is communicated with a living tissue drawing portion 70 via a connection pipe 70a. A stopper claw 74 of a cam device 73 presses against the partition plate 77 in order to keep the spring 78 compressed in the initial stage, as illustrated in FIG. 11(a).

Thereafter, once the cam device 73 rotates and the stopper claw 74 is pulled out of the cylinder (see FIG. 11(b)), the partition plate 77 is released and the spring 78 extends as illustrated in FIG. 11(c). The space between the partition plate 77 and the cylinder bottom, which is partitioned by the partition plate 77, is decompressed in accordance with the extension of the spring 78. This decompresses the inside of the living tissue drawing portion 70 via the connection pipe 70a. Accordingly, a caught tissue CE1 of the living tissue CE outside the capsule-shaped casing 1 is drawn into the living tissue drawing portion 70 via a mucous membrane aspiration port 71.

In this case, the partition plate 77 is pressed against the injection needle 75 and is moved because of the extension force of the spring 78. However, because the spring 76 absorbs the movement of the partition plate 77 temporarily and is compressed, the injection needle 75 does not protrude. Thereafter, when the spring 78 further extends, as illustrated in FIG. 11(d), the partition plate 77, the spring 76, and the injection needle 75 are collectively moved toward the living tissue drawing portion 70 and the injection needle 75 punctures the caught tissue CE1. After the puncture, the injection needle 75 stops when a medical agent ejection port 81, which is provided on the side surface of the tip of the injection needle 75, is positioned approximately at the center of the living tissue drawing portion 70 and a medical agent intake port 80, which is provided on the base portion of the injection needle 75, is positioned at the ejection port of a communication pipe 72b that communicates with a balloon 72.

In the stop position, the medical agent intake port 80 communicates with the balloon 72 and thus a medical agent 72a is pushed out by the contractile force of the balloon 72 via the medical agent intake port 80 and the medical agent 72a is injected from the medical agent ejection port 81 into the caught tissue CE1.

In Modification 2 of the third embodiment, the operations for aspirating the living tissue CE and the puncture operations of the injection needle 75 are performed using the spring 78 in the injection needle driver 79, and the timing adjustment from the aspiration operations to the puncture operations are performed using the spring 76.

The spring 78 may be compressed by the bottom portion of the injection needle 75 without the provision of the spring 76 and the partition plate 77. The timing adjustment from the aspiration operations to the puncture operations may be performed by adjusting the length of the injection needle 75. Note that it is preferable that the spring 76 and the partition plate 77 be provided because timing adjustment can be performed using the spring 76 and a compact capsule medical apparatus can be achieved.

Modification 3 of Third Embodiment

Modification 3 of the third embodiment of the present invention will be explained below. In Modification 3 of the third embodiment, drawing of the living tissue CE is detected according to Modification 1 of the first embodiment.

Figure 12:
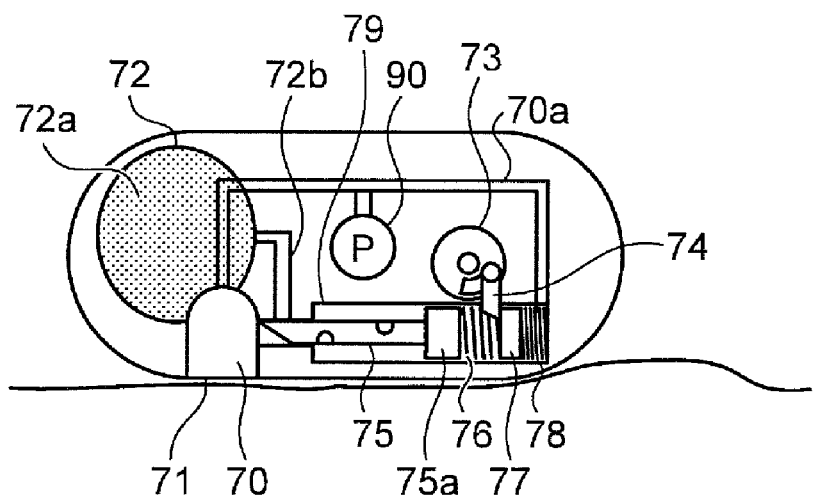
FIG. 12 is a schematic diagram of a configuration of a capsule medical apparatus according to Modification 3 of the third embodiment of the present invention.

In other words, as illustrated in FIG. 12, a detector 90 that includes a decompression pump and a pressure sensor is provided in the middle of the connection pipe 70a. Aspiration is performed by the decompression pump and the pressure during the aspiration is acquired by the pressure sensor before the operations for aspirating the living tissue CE and the puncture operations of the injection needle 75 are performed. Thus, if the pressure is lower than that before the decompression operation, it can be determined that the mucous membrane aspiration port 71 is sealed with the living tissue CE. Therefore, the cam device 73 is rotated such that the main aspiration operations are performed using the injection needle driver 79. In contrast, if the pressure does not vary from that before the decompression operations, it can be assumed that the living tissue CE is not in the vicinity of the mucous membrane aspiration port 7. Therefore, the main aspiration operations are not performed and the capsule medical apparatus is moved through guiding operations, for example, in accordance with peristalsis or by magnetic guidance.

Instead of the detector 90, various types of contact sensors, such as a pressure contact sensor or an optical contact sensor, may be provided around the mucous membrane aspiration port 71 in order to determine whether the mucous membrane aspiration port 71 is covered with the living tissue CE. When it is determined that the mucous membrane aspiration port 71 is covered, the main aspiration operations may be performed.

Modification 4 of Third Embodiment

Figure 13:
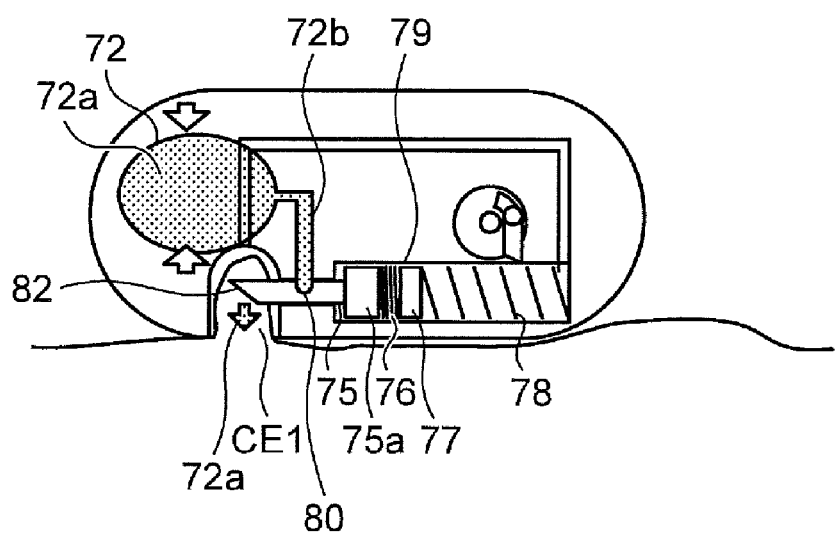
FIG. 13 is a schematic diagram of a configuration of a capsule medical apparatus according to Modification 4 of the third embodiment of the present invention.

In Modification 4 of the third embodiment, as illustrated in FIG. 13, a medical agent ejection port 82 may be provided at the tip portion of the injection needle 75.

In the drawings corresponding to the embodiments, functions, such as the imaging unit, the illuminating unit, the radio unit, the controller, the power supply, and the magnet, are omitted where appropriate.

According to the above-described embodiments, a living tissue moving unit moves a living tissue into a living tissue drawing portion, in which a space for drawing the living tissue into a body of the capsule medical apparatus is formed, and an injection needle driver causes protruding such that a port for ejecting a drug is positioned in the living tissue drawing portion and causes puncture in the living tissue in order to inject the drug. Accordingly, the drug can be injected into the desired drawn living tissue definitely.

The above and other features, advantages and technical and industrial significance of this invention will be better understood by reading the following detailed description of presently preferred embodiments of the invention, when considered in connection with the accompanying drawings.

What is claimed is:

1. A capsule medical apparatus that is introduced into a subject and injects a drug into a living tissue of the subject, the capsule medical apparatus comprising:
    a living tissue drawing portion in which a space for drawing the living tissue into a body of the capsule medical apparatus is formed;
    a living tissue moving unit that moves the living tissue into the living tissue drawing portion;
    an injection needle that has an ejection port for a drug and that protrudes such that the ejection port is positioned in the living tissue drawing portion;
    a detector that detects that the living tissue is in a position which allows the injection needle to puncture the living tissue in the living tissue drawing portion;
    an injection needle driver that drives the injection needle such that the injection needle protrudes; and
    a controller that controls the living tissue moving unit and the injection needle driver,
    wherein the controller causes the injection needle driver to drive the injection needle such that the injection needle protrudes when the detector detects that the living tissue has been drawn into the living tissue drawing portion.

2. The capsule medical apparatus according to claim 1, wherein the injection needle driver causes the injection needle to protrude such that the ejection port is positioned at approximately the center of the living tissue drawing portion.

3. The capsule medical apparatus according to claim 1, wherein the ejection port is arranged at a tip portion of the injection needle.

4. The capsule medical apparatus according to claim 1, wherein the ejection port is arranged on a side surface of the injection needle.

5. The capsule medical apparatus according to claim 1, wherein, in the space that the living tissue drawing portion forms, a depth in a direction in which the living tissue is drawn is restricted to a predetermined amount, and
the injection needle driver causes the injection needle to perform puncture in a direction approximately orthogonal to the drawing direction.

6. The capsule medical apparatus according to claim 1, wherein the living tissue moving unit draws a living tissue into the living tissue drawing portion by using a rotation mechanism.

7. The capsule medical apparatus according to claim 1, wherein the living tissue moving unit draws a living tissue into the living tissue drawing portion by using an aspiration mechanism.

8. The capsule medical apparatus according to claim 1, further comprising a magnetic member in the capsule medical apparatus.

9. The capsule medical apparatus according to claim 1, further comprising an imaging unit and an illuminating unit.

10. The capsule medical apparatus according to claim 1, wherein
the space formed by the living tissue drawing portion is defined so as to have a predetermined width orthogonal to a direction in which the living tissue is drawn, and
the injection needle driver drives the injection needle in substantially the same direction as the drawing direction of the living tissue.

11. A capsule medical apparatus that is introduced into a subject and injects a drug into a living tissue of the subject, the capsule medical apparatus comprising:
a living tissue drawing portion in which a space for drawing the living tissue into a body of the capsule medical apparatus is formed;
a living tissue moving unit that moves the living tissue into the living tissue drawing portion;
an injection needle that has an ejection port for a drug, the ejection port being positioned in the living tissue drawing portion; and
an injection needle driver that drives the injection needle, wherein moving of a living tissue by the living tissue moving unit and driving of the injection needle by the injection needle driver are performed through the same rotation operation.

12. The capsule medical apparatus according to claim 11, further comprising a magnetic member in the capsule medical apparatus.

13. The capsule medical apparatus according to claim 11, further comprising an imaging unit and an illuminating unit.

* * * * *